United States Patent
Marin Granados et al.

(10) Patent No.: US 11,918,301 B2
(45) Date of Patent: Mar. 5, 2024

(54) OCULAR GONIOMETER

(71) Applicants: Universidad de Malaga, Malaga (ES); Salvador Nebro Cobos, Malaga (ES)

(72) Inventors: Manuel D Marin Granados, Malaga (ES); Oscar D De Cozar Macias, Malaga (ES); Juan Antonio Bascunana Pareja, Malaga (ES); Joaquin Fernandez Cabrera, Malaga (ES); Salvador Nebro Cobos, Malaga (ES)

(73) Assignee: UNIVERSIDAD DE MALAG, Malaga (ES)

( * ) Notice: Subject to any disclaimer, the term of this patent is extended or adjusted under 35 U.S.C. 154(b) by 602 days.

(21) Appl. No.: 17/059,760

(22) PCT Filed: May 31, 2019

(86) PCT No.: PCT/ES2019/070368
§ 371 (c)(1),
(2) Date: Nov. 30, 2020

(87) PCT Pub. No.: WO2019/229287
PCT Pub. Date: Dec. 5, 2019

(65) Prior Publication Data
US 2021/0205024 A1     Jul. 8, 2021

(30) Foreign Application Priority Data
May 31, 2018   (ES) ................. ES201830519

(51) Int. Cl.
*A61B 34/20*     (2016.01)
*A61B 3/117*     (2006.01)
(Continued)

(52) U.S. Cl.
CPC .............. *A61B 34/20* (2016.02); *A61B 3/117* (2013.01); *A61B 5/1071* (2013.01); *A61B 90/39* (2016.02);
(Continued)

(58) Field of Classification Search
CPC ..... A61B 3/117; A61B 5/1071; A61B 5/6821; A61B 34/20; A61B 90/30; A61B 90/39;
(Continued)

(56) References Cited

U.S. PATENT DOCUMENTS

2008/0228210 A1    9/2008  Davis

FOREIGN PATENT DOCUMENTS

WO    2010118469 A1    10/2010
WO    2011126938 A1    10/2011
(Continued)

OTHER PUBLICATIONS

Salvador Nerbo Cobos, "Goniómetro ocular Clinica Oftalmológica Nebro", video, Jan. 27, 2019, YouTube [retrieved on Aug. 30, 2019]. <https://www.youtube.com/watch?v=8M_OwxqDOJg>.

*Primary Examiner* — Jack Dinh
(74) *Attorney, Agent, or Firm* — Hayes Soloway PC (57) ABSTRACT

The invention relates to a goniometer that enables precise marking of the desired ocular axis in the phase immediately after surgery for the treatment of astigmatism. It essentially consists of two circular, transparent discs, one of which is at least axially stationary, in which the angles from 0° to 180° are marked, which are aligned with the angles from 0° to 180° of the patient's eye; and the other one of which is movable both angularly and axially, with a reference mark (9) and moving rigidly connected to a marking part (12), impregnated with die, which is responsible for marking the eye. Not only does the device make it possible to carry out said marking in a precise and comfortable manner, it also (Continued)

makes it possible to measure the angle of toric lenses already implanted.

4 Claims, 6 Drawing Sheets

(51) Int. Cl.
    *A61B 5/107*     (2006.01)
    *A61B 90/00*     (2016.01)
    *A61F 2/16*     (2006.01)
    *A61F 9/007*     (2006.01)

(52) U.S. Cl.
    CPC ............ *A61F 2/1645* (2015.04); *A61F 9/007* (2013.01); *A61B 2034/2068* (2016.02); *A61B 2090/3908* (2016.02); *A61B 2090/3983* (2016.02)

(58) Field of Classification Search
    CPC .. A61B 2017/00734; A61B 2034/2068; A61B 2090/067; A61B 2090/3908; A61B 2090/395; A61B 2090/3983; A61B 2560/0431; A61F 2/1645; A61F 9/007
    See application file for complete search history.

(56) References Cited

FOREIGN PATENT DOCUMENTS

| WO | 2014072342 A1 | 5/2014 |
|---|---|---|
| WO | 2014129977 A1 | 8/2014 |

OCULAR GONIOMETER

CROSS-REFERENCE TO RELATED APPLICATIONS AND PRIORITY

This patent application claims priority from PCT Patent Application No. PCT/ES2019/070368 filed May 31, 2019, which claims priority from Spanish Patent Application No. ES P201830519 filed May 31, 2018. Each of these patent applications are herein incorporated by reference in its/their entirety.

TECHNICAL FIELD

The present invention refers to an ocular goniometer, the purpose of which is to perform a precise marking of the desired ocular axis in the immediate phase of the surgery for the treatment of astigmatism in the operating room with the patient seated and the head in an upright position.

The device of the invention allows visualizing simultaneously the patient's eye over its entire anterior surface and the measurement angles, so that the surgeon can correctly position the device and make the 0°-180° axis of the patient's eye coinciding with that of the goniometer.

Also, it can be used to measure the precise position in which the lens is placed in the postoperative period and quantify possible misalignments of the toric lens, which are responsible for the appearance of unwanted astigmatisms after surgery.

Additionally, the invention can be used to measure any axis in the anterior part of the eye for any eventuality in which such a procedure is required.

BACKGROUND OF THE INVENTION

Currently, there is the possibility of eliminating astigmatism in cataract surgery patients through the implantation of toric intraocular lenses. These lenses do not have the same power in all their axes and when placed in the correct position, they can correct the patient's corneal astigmatism.

Currently, there are toric monofocal and multifocal lenses, with a significant number of patients being the potential beneficiaries of their surgical implant.

The preoperative calculations of the lens to be implanted, known in ophthalmology as Biometry, are currently very precise, indicating the power of the lens and in the case of using a toric lens, the axis in which said lens must be placed.

Once in the surgical room with the calculations obtained, it is necessary to mark the axis in the eye in which the toric lens should be placed. This marking must be carried out with the patient in an upright position, to avoid a rotation of the eye that appears when lying in a supine position and which would distort the marking of the axis. It must also be very precise, since, if we deviate a few degrees, the effectiveness of the surgical correction of astigmatism will decrease. In the final phase of cataract surgery, when implanting the lens, the mark on the axis made in the eye is to be matched with the mark on the toric lenses, ensuring that it is in the correct position.

To carry out this marking, there are currently two modes manually, and through automatic systems.

In the case of manual marking, it is performed in two steps. In a first step, the axis 0°-180° is marked with the position of the patient's upright head, and in a second step, already lying on the operating table, the desired axis in which the lens is to be implanted is marked. Marking can be done with a marker, aided by an angle meter, whose mark is usually coarse, being not very precise.

In the case of automatic marking, sophisticated image guidance systems are used for it. These systems capture the appearance of the anterior part of the eye with the patient in an upright position, and calculate the location of the desired axis, matching it with anatomical details of the eye. Once on the operating table, they locate these anatomical details and project the virtual image of the axis where the lens is to be implanted on the surgical microscope, making a virtual marking.

Document WO2011126938A1 discloses an apparatus for marking the axis of astigmatism in the immediate phase to the surgery for the implantation of a corrective toric lens. The apparatus comprises a contact element with the eye that can be rotated relative to a reference piece incorporating the angle markings. The rotation of the marking element can be carried out by the user thanks to a thread that protrudes at the rear end of the device and which is connected to the marking part, so that said marking part rotates integrally with the thread until positioned at the desired angle measured on the reference piece. The central axis of the apparatus is hollow. Thus, the user can look through the turning thread and see the surface of the patient's eye to properly align the apparatus.

The problem with this device is that the scanner cannot observe the patient's eye and the angles of the reference piece marked on the outside at the same time. This makes it impossible to measure an axis of an already implanted toric lens.

In the same way, the field of the observer is very small, in addition to not having lighting means, working in unfavorable conditions.

All this makes the maneuver uncomfortable and imprecise.

For its part, document US2008228210 A1 describes a device for marking the axis of astigmatism that consists of a marking device incorporated in a lens trial frame. The frame contains a fixed piece of reference to indicate the angles. The marking device incorporates an outer hollow cylindrical piece that ends in the shape of a disc and that houses the marking piece inside, so that the outer disc is inserted into the frame in the space of the lens and can be rotated to select the angle of the axis to be marked in the eye by matching an existing mark on the disk with the value of said angle on the graduated piece of the frame. The marking of the eye is carried out by means of the dye impregnated marking piece which can be displaced in a counter posterior direction to move it towards the surface of the eye by rods which are inserted into longitudinal grooves of the outer cylindrical part.

Also, these rods are used to rotate the marking piece to the desired angle. The apparatus also incorporates an illumination source, a battery and a switch and can allow direct inspection of the eye surface by the surgeon through the distal end.

The problem with this device is that, although the scanner can inspect the maneuver, it must be done in a complex way, since it does not have a display screen.

Similarly, trial fames can be easily moved and mislead the marking. By rotating the rods to advance the cylindrical marking piece, the desired axis can be moved, resulting in a slow maneuver, being subject to more sources of error, since lengthening the maneuver makes it easier for the patient to move the eye or move the trial frame.

Similarly, this device does not allow measuring the axis of an already implanted toric lens.

Finally, document WO2010118469 A1 describes a simple apparatus for aligning an intraocular toric lens with the axis of astigmatism of a patient. Said apparatus comprises a lower disc, in contact with the patient's eye, and a posterior or distal surface with angle markings. The apparatus comprises means that allow the surgeon to have in view at the same time the angle markings and the eye of the patient in which the axis marking has previously been performed.

This apparatus is not designed to perform the marking in the eye but to correctly position the toric lens in a subsequent step after marking, nor does it allow measuring the axis of a toric lens already implanted toric lens.

EXPLANATION OF THE INVENTION

The proposed ocular goniometer fully satisfactorily solves the aforementioned problem, based on a simple but effective solution.

For this, and more specifically, the goniometer consists of two circular discs, both transparent. A fixed one, at least angularly, in which the angles from 0° to 180° are marked, which we will make coincide with the angles from 0° to 180° of the patient's eye. This element does not rotate.

The second circular element is superimposed on the first, being more anterior, and can rotate with respect to the first circular disc. In such a way that it allows us to choose the desired axis to mark it, as it has a reference mark. This second element moves, either with respect to the first with an anteroposterior movement by activating a spring from the handle, in such a way that when pressing it moves forward, approaching the eye and can make the marking, and once done, move away from it; either in conjunction with the first by means of a gear/rack mechanism activated by a trigger, in such a way that when pressed they move forward, approaching the eye and can perform the marking, and once done, move away from it.

In the front part of said circular element protrudes the axis where the marking piece will be fitted.

The marking piece marks a diameter of the sphere, as it is engaged in the second element, and being able to rotate it, we can choose the axis that interests us to carry out the marking since it coincides with the reference mark and is rotated integrally with the second disc.

The marking piece is disposable and not reusable, and is impregnated with ink in its anterior part, wrapped in a cartridge that guarantees its sterility and the stability of the dye.

In this way, after removing the wrapping from the marking piece and fitting it into the circular element, we can rotate said element to choose the appropriate axis and advance it so that the marking piece contacts the eyeball performing said marking with a high precision.

The advancement of the piece is achieved either by pressing the button designed for this purpose and transmitting a hydraulic pressure inside the axis that causes the terminal portion thereof to move, where the second wheel is crimped, with respect to the proximal portion, where the first is crimped, for being telescopic. Alternatively, said advancement is achieved by means of a gear/rack mechanism. Thus achieving an anteroposterior movement, either of the second wheel with respect to the first, or of both together. When the pressure is released the system returns to its rest position.

The goniometer also has a handle to grip it and facilitate the surgeon's task.

Inside there is a battery. On the outside there is a gear wheel to choose the desired axis, a button to advance the second circular element and the marking piece, and an on/off button to turn on the bulb that illuminates the goniometer from the inside and the display screen.

In the part closest to the explorer there is a display screen through which the explorer observes the patient's eye, as well as the two discs, to ensure correct marking, ensuring that the patient is looking at the fixation point (red light bulb) and that we are doing the correct maneuver, as we are observing the eye and the angles.

Inside there is a bulb, for example, a micro LED, with red light to fix the patient's gaze, and a bulb that provides light to visualize the operation.

To measure the angle at which a toric lens is implanted, simply match the reference mark on the second disc with the mark on the toric lens and take the reading.

The following advantages are derived from this structuring:

Compared to automatic systems:

The automatic systems are very expensive, involving the use of very sophisticated surgical microscopes. They also need to occupy a physical space that is not always available and they are not portable. The ocular goniometer would have a much lower cost, occupies a minimal space and is portable and can be used in any operating room.

Compared to manual systems:

The marking is carried out in a single step, minimizing errors and avoiding annoying maneuvers for the patient. At the same time, the measurement and marking are much more precise, the ink mark occupying a fine line, and not a diffuse stain like a marker mark.

BRIEF DESCRIPTION OF THE DRAWINGS

To complement the description that is going to be carried out below and in order to help a better understanding of the characteristics of the invention, according to a preferred example of a practical embodiment thereof, a set of drawings is accompanied as an integral part of said description, where, for illustrative and non-limiting purposes, the following has been represented.

EXAMPLES OF EMBODIMENT OF THE INVENTION

Figure 1:
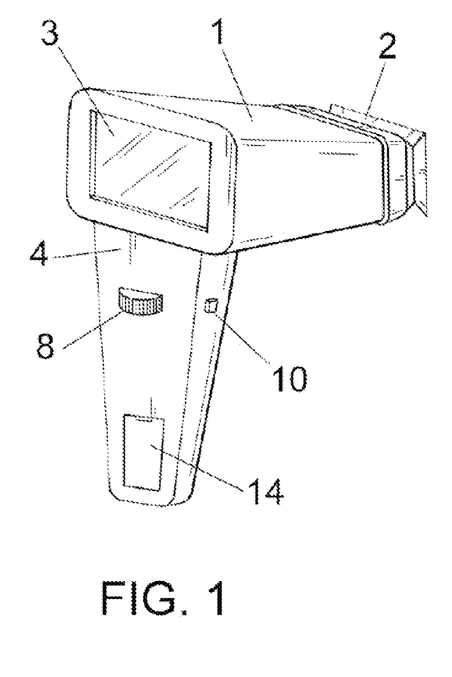
FIG. 1 shows a view of an ocular goniometer made according to the present invention.
Figure 2:
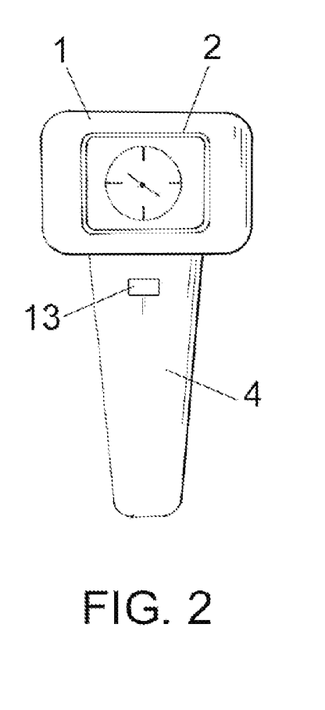
FIG. 2 shows a front elevation view of an ocular goniometer made in accordance with the present invention.
Figure 3:
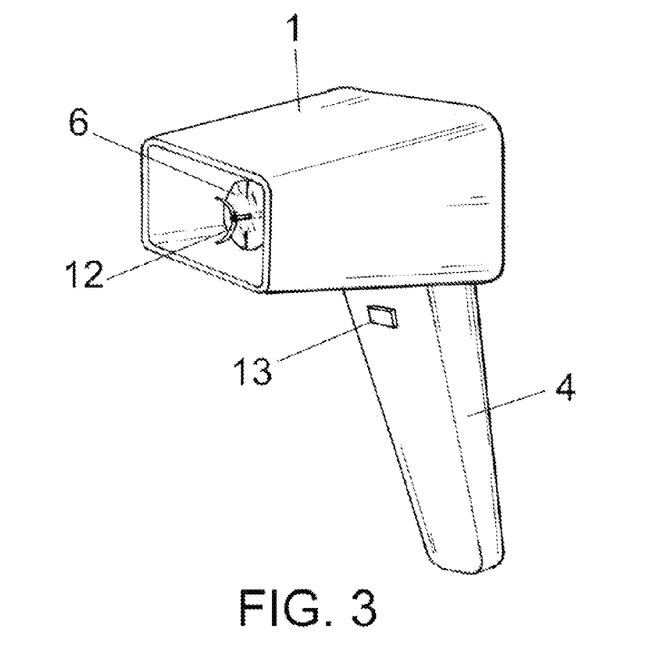
FIG. 3 shows a front-side perspective view of an ocular goniometer made according to the present invention.

In view of the figures outlined, and especially of FIGS. 1 to 3, it can be seen how the ocular goniometer is made up of a body or casing (1) open at its ends, at whose anterior end it is established a flexible rubber piece (2) to adapt and stabilize the patient's physiognomy, while at its rear end it includes a display screen (3), ending at the bottom in a handle (4), with a series of controls.

Figure 4:
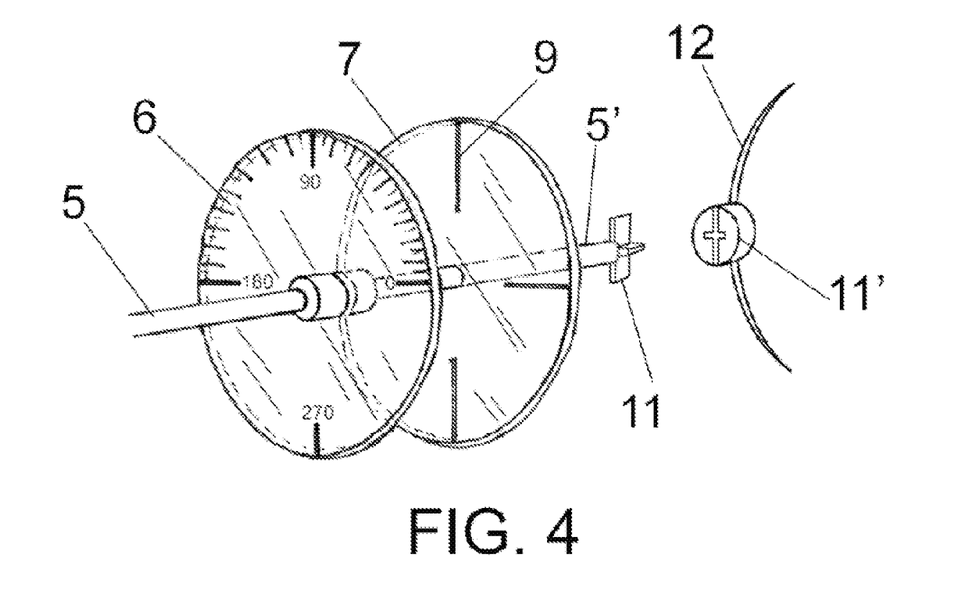
FIG. 4 shows a detail in perspective of the arrangement of the graduated guide discs and the anchoring of the marking piece on the corresponding axis.
Figure 5:
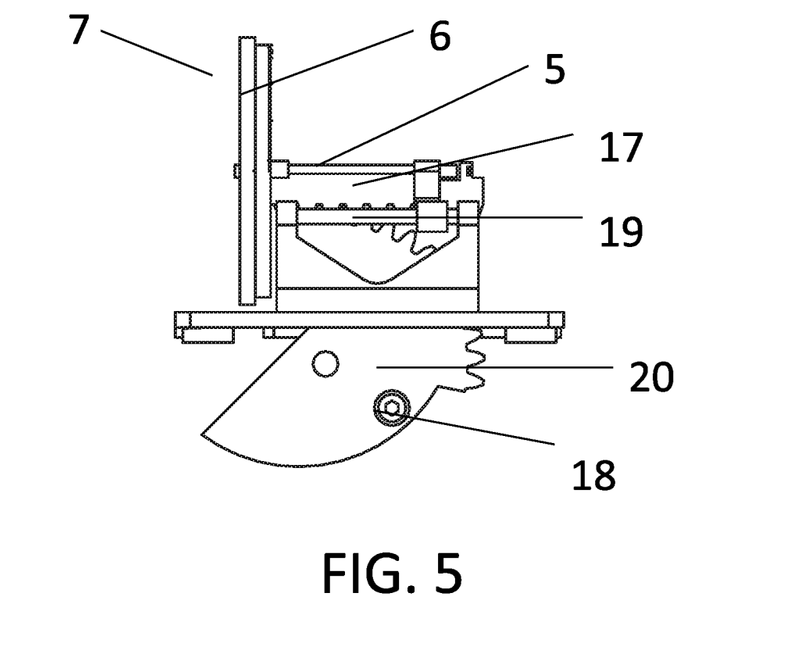
FIG. 5 shows a side view of the arrangement of the graduated discs and of the gear/rack mechanism that allows axial displacement of both in an ocular goniometer made according to the present invention.
Figure 6:
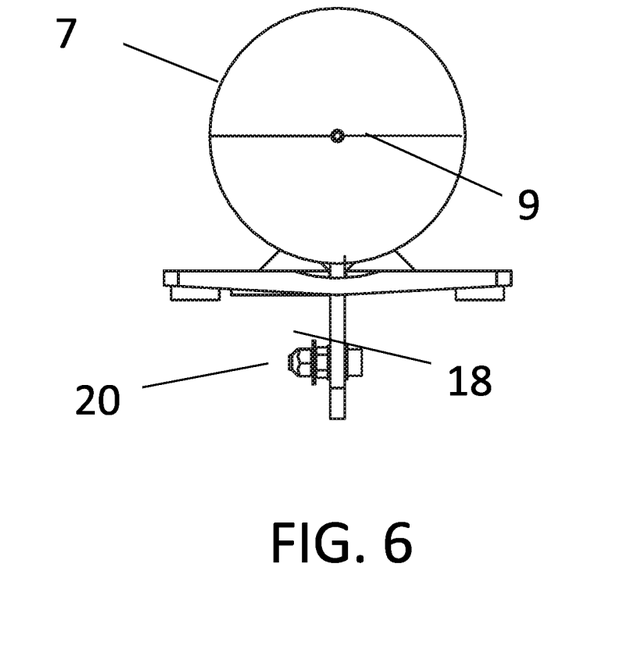
FIG. 6 shows a front view of the arrangement of the graduated discs and of the gear/rack mechanism that allows axial displacement of both in an ocular goniometer made according to the present invention.
Figure 7:
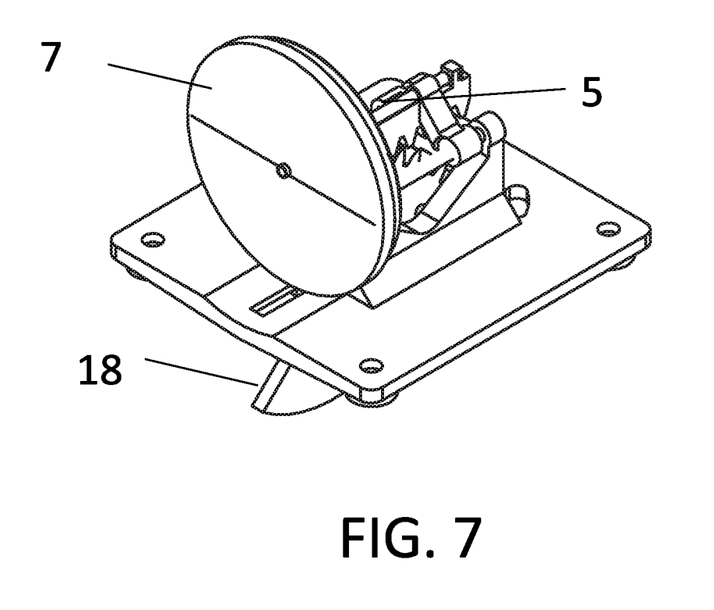
FIG. 7 shows a front perspective of the arrangement of the graduated discs and the gear/rack mechanism that allows axial displacement of both in an ocular goniometer made according to the present invention.
Figure 8:
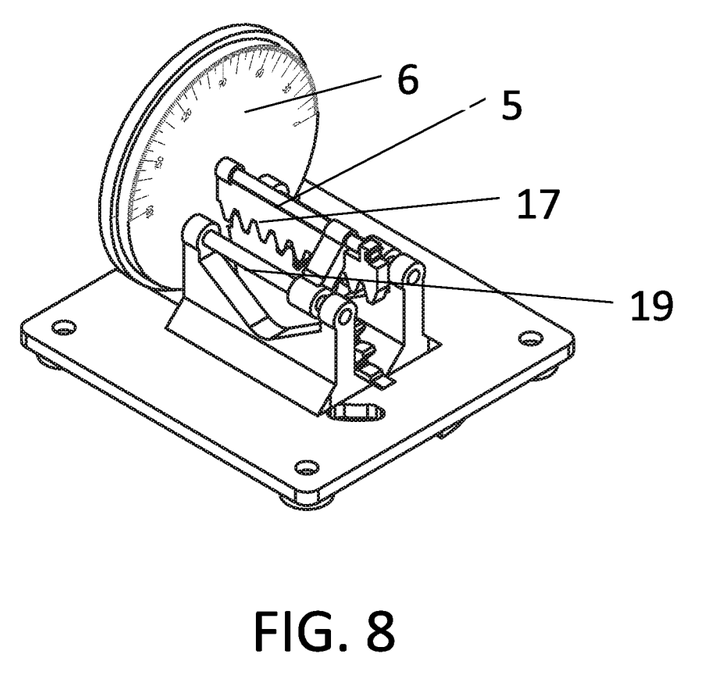
FIG. 8 shows a rear perspective view of the arrangement of the graduated discs and the gear/rack mechanism enabling axial displacement of both in an ocular goniometer made in accordance with the present invention.
Figure 9:
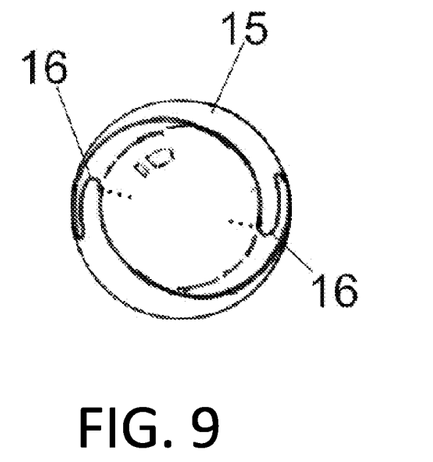
FIG. 9 shows a front elevation view of the toric lens in place.
Figure 10:
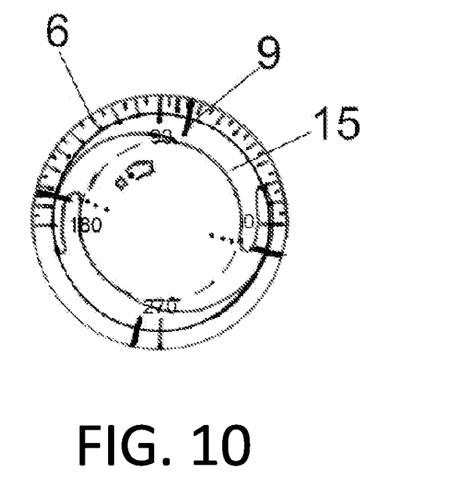
FIG. 10 shows a front elevation view of the toric lens placed with superposition of the optical goniometer.
Figure 11:
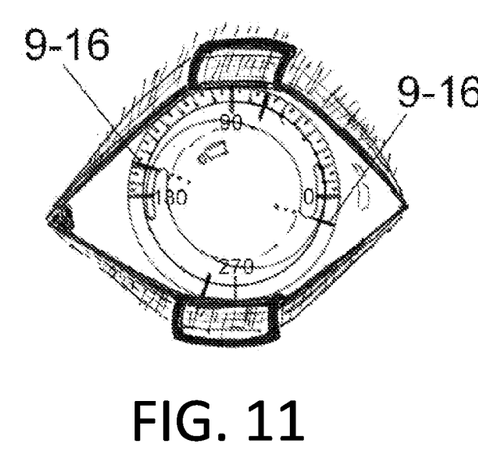
FIG. 11 shows a front elevation view of the position reading of the toric lens.
Figure 12:
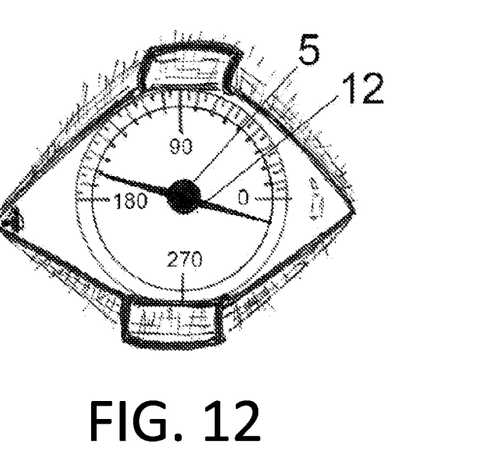
FIG. 12 shows a front elevation view of the marking from the display screen.

In an ocular goniometer made according to the present invention, an axis (5) is established within the casing (1), associated with two circular discs, both transparent. The first disc (6) is fixed, and the angles from 0° to 180° are marked on it, which we will make coincide with the angles from 0° to 180° of the patient's eye. Consequently, this element neither rotates nor moves. For its part, the second disk (7) is superimposed above the first, and can rotate with respect to the first circular disc, through any conventional mechanism. The rotation of said second disc (7) can be controlled, for example, through a gear wheel (8) present on the handle (4), allowing to choose the desired axis to mark, since it has reference marks (9) (FIGS. 4, 8 and 9), for example, a line of sight (FIGS. 5 and 6). As shown in FIG. 4, in order to allow the second disc (7) to be moved with respect to the first (6), the axis (5) has a telescopic nature, and the movement, which is carried out through a pushbutton (10) present on the handle, is carried out against the tension of a spring (not represented in the figures) that makes the second disk (7) tend to the position of maximum proximity with respect to the first disc (6). The telescopic rod (5') of the axis (5) is finished off in an anchor (11) complementary to an anchor (11') provided by the marking piece (12).

In an ocular goniometer made according to the present invention, an axis (5) associated with two circular and transparent discs is established within the casing (1), a first disc (6) fixed angularly, on which angles are marked from 0° to 180°, and a second disc (7), with a reference mark (9) and superimposed anteriorly to the first, integral to the axis (5), axis associated with a rack-support (17) with which a trigger is engaged (18) when it is actuated and rotates around an axis available in the handle (4) of the device; having provided that the end of the axis (5) is finished off with a marking piece (12) aligned at all times with the reference mark (9) provided on the second disc (7), rotating jointly with it. The axis (5), being hollow, allows the passage of light. The mechanism, set formed by the axis (5), the rack-support (17) and the two discs (6, 7), moves on two guides (19); the rack-support (17) slides through said guides (19), which are attached to the base of the casing (1) by means of two supports. The return of the mechanism is achieved by the action of a traction spring attached to the trigger (18) in a screw that acts as a support (20); the other end of the spring is attached to an internal protrusion of the handle.

The marking piece (12) marks a diameter of the sphere, remaining aligned at all times with the mark provided on the second disc (7), rotating jointly with it.

As previously mentioned, said marking piece (12) is disposable and not reusable, and is impregnated with ink in its anterior part, wrapped in a cartridge that guarantees its sterility and the stability of the dye.

Thus, and after removing the wrapping from the marking part and fitting the anchor (11) through the anterior window of the casing (1), we can rotate said element to choose the appropriate axis and advance it so that the part of marking contact with the eyeball performing such marking with high precision.

Finally, it only remains to point out that the device will incorporate a pair of lighting elements, specifically a red reference light, of low power, for example, a micro LED diode, whose emission passes through the interior of the axis (5), to that the patient fixes his or her gaze on that point, and an illumination bulb that allows the work area to be illuminated and therefore work in optimum conditions. For this, and as is evident, the device will have batteries or batteries, which will preferably be arranged in a compartment (14) provided in the handle (4), also having an on/off button (13), visible in FIGS. 2 and 3.

According to FIGS. 9 to 12, to measure the angle at which a toric lens (15) is implanted, it would be enough to make the reference mark (9) of the second disc (7) coincide with the mark (16) of the toric lens and do the reading.

The invention claimed is:

1. An ocular goniometer, characterized in that it is made from a body or casing open at its ends, which at its rear end is finished off in a display screen, internally including a handle, with a series of controls, with the particularity that an axis, associated with two circular and transparent discs, is established within the casing, a first disc angularly fixed, on which the angles are marked from 0° to 180°, and a second disc, with a reference mark and superimposed above the first, integral with the axis, axis associated with a rack-support with which a trigger is engaged when it is actuated and rotates around an axis available on the handle of the device; having provided that the end of the axis is finished off with a marking piece aligned at all times with the reference mark provided on the second disc, rotating integrally with it; also provided with a reference light for the patient's eye, and lighting means for the work area.

2. The ocular goniometer, according to claim 1, characterized in that the casing is finished off at its anterior end in a flexible rubber piece for adaptation and stabilization to the physiognomy of the patient.

3. The ocular goniometer, according to claim 1, characterized in that the reference light materializes in a small red light, while the lighting means materialize in a bulb, the device having a compartment in its grip for an electrical power source, such as a battery or a set of batteries, electronic assisted by an on/off button, arranged on the handle.

4. The ocular goniometer, according to claim 1, characterized in that the marking piece is disposable and not reusable, being impregnated with ink in its anterior part, being supplied wrapped in a cartridge that guarantees its sterility and the stability of the dye.

* * * * *